United States Patent [19]

Lukác et al.

[11] Patent Number: 4,661,641
[45] Date of Patent: Apr. 28, 1987

[54] SUBSTITUTED ALKYNES USEFUL AS INTERMEDIATES IN THE SYNTHESIS OF CAROTENOIDS

[75] Inventors: Teodor Lukác, Aesch; Milan Soukup, Stein; Erich Widmer, Münchenstein, all of Switzerland

[73] Assignee: Hoffmann-La Roche Inc., Nutley, N.J.

[21] Appl. No.: 614,607

[22] Filed: May 29, 1984

[30] Foreign Application Priority Data

Jun. 9, 1983 [CH]  Switzerland ......................... 3153/83
Oct. 13, 1983 [CH]  Switzerland ......................... 5583/83

[51] Int. Cl.[4] .................... C07C 31/135; C07C 31/20; C07C 53/134
[52] U.S. Cl. .................................. 568/377; 568/379; 568/825; 568/838; 568/61; 560/121; 560/126
[58] Field of Search ............... 568/825, 377, 379, 838; 260/463

[56] References Cited

U.S. PATENT DOCUMENTS 2,931,828  4/1960  Prost .................................. 260/463
2,993,864  7/1961  Monroe et al. ..................... 260/463
4,219,506  8/1980  Olson et al. ........................ 568/496

FOREIGN PATENT DOCUMENTS 2558806  7/1977  Fed. Rep. of Germany .

OTHER PUBLICATIONS

Loeber et al., J. Chem. Soc. (C) pp. 404–408, 1971.

Baumann et al., Liebigs Ann. Chem., pp. 1945–1951, 1979.

Primary Examiner—Donald G. Daus
Assistant Examiner—Stephen M. Kapner
Attorney, Agent, or Firm—Jon S. Saxe; George M. Gould; William H. Epstein

[57] ABSTRACT

Compounds of the formula

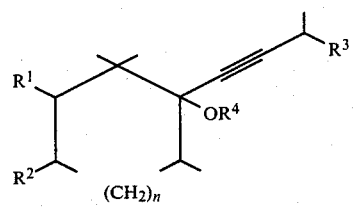

I wherein n is either 0 or 1; $R^1$ and $R^2$ is hydrogen and the other is hydrogen, hydroxy, oxo group, a protected hydroxy or protected oxo group; $R^3$ is hydroxy oxo group, $=CH-CH_2-OH$, $=CH-CHO$ or one of the foregoing groups where the hydroxy or oxo functions are protected; $R^4$ is $-CO-OR^6$, $-CO-R^6$, $-CO-NR^6R^7$, $-CO-Cl$ or $-SO_2-R^6$; $R^6$ is saturated or aromatic hydrocarbon; and $R^7$ is saturated or aromatic hydrocarbon or hydrogen, are converted by cleavage of $R^4OH$ into corresponding cycloalkenes and protecting groups, if present, are hydrolyzed.

The compounds obtained are valuable intermediates in carotenoid syntheses.

11 Claims, No Drawings

SUBSTITUTED ALKYNES USEFUL AS INTERMEDATES IN THE SYNTHESIS OF CAROTENOIDS

SUMMARY OF THE INVENTION

In accordance with this invention, it has been discovered that compounds of the formula

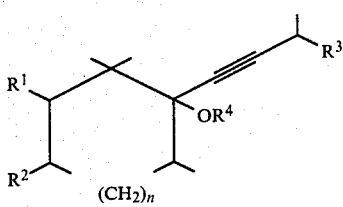

I wherein n is either 0 or 1; one of $R^1$ and $R^2$ is hydrogen and the other is hydrogen, hydroxy, oxo group, a protected hydroxy or protected oxo group; $R^3$ is hydroxy, oxo group, =CH—$CH_2$—OH, =CH—CHO or one of the foregoing groups where the hydroxy or oxo functions are protected; $R^4$ is —CO—$OR^6$, —CO—$R^6$, —CO—$NR^6R^7$, —CO—Cl or —$SO_2$—$R^6$; $R^6$ is saturated or aromatic hydrocarbon; and $R^7$ is saturated or aromatic hydrocarbon or hydrogen, can be converted by cleavage of $R^4OH$ into a compound of the formula

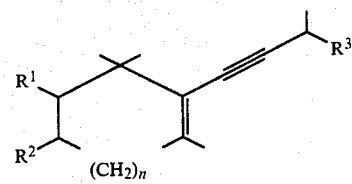

II wherein n, $R^1$, $R^2$ and $R^3$ is as above, and, if a compound of formula II contains a protected hydroxy or oxo group then by hydrolysis converting to the corresponding hydroxy or oxo compound.

DETAILED DESCRIPTION

As used throughout this application, the term "protected hydroxy or oxo group" or "protected hydroxy or oxo function" means any conventional organic protecting group which upon hydrolysis yields the hydroxy or oxo group. Any conventional hydrolyzable protecting group which is generally used to protect oxo or hydroxy groups can be used in accordance with this invention. Exemplary hydroxy protecting groups are the ether, silyl ether and acetal containing 1 to 7 carbon atoms such as methoxy, ethoxy, benzyloxy, trimethylsilyloxy and (2-methoxy-2-propyl)oxy. Exemplary oxo protecting groups are the acetal or ketal groups, containing 1 to 10 carbons, particularly those derived from alkanols and alkanediols. Preferably the term "protected oxo group" stands for 2 methoxy groups or for an ethylenedioxy group.

The term "saturated or aromatic hydrocarbon group" as used herein means any conventional saturated hydrocarbon group and any conventional aromatic hydrocarbon. The term "saturated hydrocarbon" as used herein designates a saturated aliphatic straight or branched chain hydrocarbon containing from 1 to 10 carbon atoms such as ethyl, methyl, isopropyl etc. The term "aromatic hydrocarbon" as used throughout the specification designates a cyclic hydrocarbon having an aromatic ring such as aryl and arylalkyl groups. The term "aryl" designates mononuclear aromatic hydrocarbon groups such as phenyl, tolyl, which can be unsubstituted or substituted in one or more positions with a lower alkyl or substituent and polynuclear aryl groups such as naphthyl, anthryl, phenanthryl, which can be unsubstituted or substituted with one or more of the aforementioned groups. The preferred aryl groups are the substituted and unsubstituted mononuclear groups particularly phenyl or tolyl. The term "arylalkyl" designates arylalkyl groups where aryl is defined as above and alkyl is preferably lower alkyl. The term "lower alkyl" means a saturated aliphatic straight or branched chain hydrocarbon containing from 1 to 7 carbon atoms such as ethyl, methyl, isopropyl, etc.

In accordance with the present invention it was discovered that compounds of formula I can be converted under mild conditions and in good yield into pure compounds of Formula II.

In accordance with this invention the compound of formula I is converted to the compound of formula II by cleaving off $R^4OH$ of compound I either by heating and/or catalyst. The term "cleaving" as used herein means the splitting or separation of the alcohol moiety from the starting compounds through any conventional method to achieve alcohol separation. The preferred methods of cleaving are heating and/or by catalyst. Any conventional catalyst can be utilized. Suitable catalysts are, for example: (a) organic nitrogen bases, especially primary and secondary nitrogen bases such as nitrogen containing heterocyclic compounds (e.g. imidazole, 1,2,4-triazole, aniline); (b) salts of organic nitrogen bases with strong acids (preferably acids with $pK_a<1$), especially chlorides, bromides and tosylates (e.g. pyridinium p-tosylate); (c) phosphonium salts (e.g. triphenylphosphonium chloride orbromide); (d) acids, preferably strong acids with $pK_a<1$ (e.g. toluenesulphonic acid, Amberlyst A 15 ® (Fluka AG) [which is a strongly acid cationic ion-exchange resin], hydrochloric acid, sulphuric acid); (e) trialkylchlorosilanes (e.g. trimethylchlorosilane); (f) lithium salts, for examples lithium salts of strong ($pK_a<1$) acids (e.g. lithium chloride, lithium perchlorate, lithium tetrafluoroborate); and, (g) palladium-(O) catalysts (e.g. by the addition of palladium acetate).

In accordance with this invention the cleavage of $R^4OH$ already takes place under mild conditions, the optimum reaction temperature being dependent inter alia on the meaning of $R_4$ and on the catalyst, which may optionally be used. In some cases $R^4OH$ is cleaved off already at room temperature, e.g. when $R^4$ is —CO—$OCH_3$ and lithium perchlorate is used as the catalyst. On the other hand, temperatures up to 200° C. or higher temperatures can be used. However, high temperatures are undesirable, if the reaction is carried out on a technical scale, and some decomposition of the product may occur during long pre-heating periods. Therefore, the cleavage of $R^4OH$ is carried out preferably below about 200° C., most preferably below about 160° C. Optimum reaction temperatures can easily be found by experiment on a case to case basis.

The cleavage of $R^4OH$ when carried out in the presence of a catalyst may be carried out at room temperature or at higher temperatures. The catalysts which may be used are as described above. Catalysts can be used in conventional catalytic amounts or greater amounts. In carrying out this reaction, the pressure is not critical and this reaction can be carried out at atmospheric pressure. The catalytic cleavage is generally carried out at temperatures from room temperature to about 200° C. The preferred temperature range is from room temperature to about 160° C. In accordance with this embodiment, it is also preferred to vary the temperature at which the reaction is carried out in accordance with the substituent chosen as $R^4$. For example, if $R^4$ is $-CO-OCH_3$ or $-CO-OC_2H_5$ then the preferred temperature range will be from room temperature to about 100° C.

According to another embodiment of this invention, the process for converting the compound of formula I to the compound of formula II can be carried out without catalyst by heating, i.e. heating the compound of formula I to a temperature of from about 150° to 200° C. In accordance with this embodiment, it is preferred to vary the temperature at which the reaction is carried out in accordance with the substituent chosen as $R^4$. For example, if $R^4$ is $-CO-OCH_3$ or $-CO-OC_2H_5$ then the preferred temperature will be from 160° to 190° C. In carrying out this reaction, the pressure is not critical and this reaction can be carried out at atmospheric pressure.

In carrying out this reaction, any conventional inert organic solvent can be used. Exemplary inert organic solvents are ether, alcohol, nitrile, amide, or a saturated, aromatic or chlorinated hydrocarbon. Preferred solvents are diethyl ether, tetrahydrofuran, ethylene glycol dimethyl ether, diethylene glycol dimethyl ether, triethylene glycol dimethyl ether, methanol, acetonitrile, dimethylformamide, hexane, toluene, benzene, xylene, methylene chloride, dichloroethane and the like.

Any conventional method of hydrolysis of the protecting groups can be used when $R^1$, $R^2$ or $R^3$ of compound II is or contains a protected hydroxy or oxo group.

Where $R_3$ of compound I is a $=CH-CH_2OH$ a preferred reaction is carried out in the presence of equimolar or higher amounts of phosphonium salt, preferably triphenylphosphonium chloride or bromide. A corresponding compound of formula II is formed which is converted directly to the corresponding phosphonium salt (i.e. the hydroxy group in $R^3$ is converted into a phosphonium salt group, such as $-P(C_6H_5)_3{}^+Cl^-$ or $-P(C_6H_5)_3{}^+Br^-$.

In accordance with this invention preferred compounds of formula I are those where n is 0 and $R^2$ is hydrogen and those where n is 1. An especially preferred compound of formula I is one where n is 1 and $R^1$ is hydrogen. Further, those compounds of formula I are preferred in which one of $R^1$ or $R^2$ is hydrogen and the other is hydrogen or hydroxy, especially hydroxy, such as, for example, the compounds of formula I in which n is 1, $R^1$ is hydrogen and $R^2$ is hydroxy.

Especially preferred groups for $R^3$ are hydroxy and $=CH-CH_2-OH$. In addition, double bonds when present in $R^3$ preferably have the trans configuration.

Especially preferred groups for $R^4$ in formula I are the groups $-CO-OR^6$, especially those in which $R^6$ is $C_1-C_6$-alkyl. Particularly preferred are $-CO-OCH_3$ and $-CO-OC_2H_5$. Other preferred groups for $R^4$ in formula I are $-CO-R^6$, especially those in which $R^6$ signifies an aromatic hydrocarbon group (e.g. benzoyl).

Further preferred are those compounds of formula I in which the hydrogen atom in the 5-position of the cyclopentyl ring or in the 6-position of the cyclohexyl ring and the $R^4O-$ group are in the cis position to one another (syn elimination).

In accordance with this invention another embodiment is the reaction converting a compound of the general formula

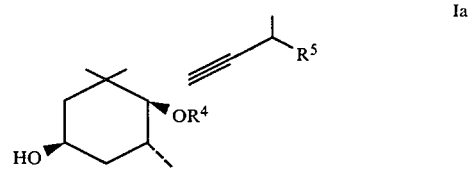

wherein $R^5$ is hydroxy or $=CH-CH_2-OH$ and $R^4$ is as above, or the optical antipode thereof by cleavage of $R^4OH$ in the presence of a basic sterically hindered lithium compound into a compound of the general formula

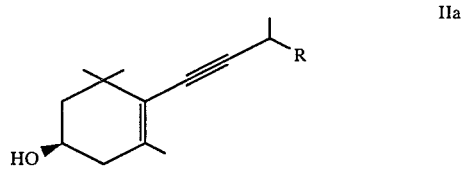

wherein $R^5$ is as above,
or the optical antipode thereof.

The term "basic sterically hindered lithium compounds" means any conventional organolithium compounds which have steric hindrance on the basic group (in order to avoid nucleophilic attack on the group-$OR^4$) and which are derived from organic compounds with $pK_a$ values of at least about 9, preferably at least about 11. The steric hindrance can be effected, for example, by branching or substitution at the carbon atom in the 1-position or by substitution in the ortho-position of a benzene ring. Preferred among such compounds are alkyl lithiums, lithium alkanolates, lithium phenolates, lithium dialkylamides and the like which fulfill the above conditions, for example lithium tertbutylate, lithium 1,1-dimethylpentanolate, lithium 2,6-dimethylphenolate, lithium 2,6-di(tert.-butyl)phenolate, lithium 2,6-dichlorophenolate, tertbutyl lithium, 2,6-di(tert.butyl)phenyl lithium and lithium diisopropylamide.

In this embodiment approximately 2 mol of lithium compound at a minimum are used per mol of compound of formula Ia (or antipode thereof). In a preferred embodiment about 2-3 mol equivalents of lithium compound are used, although higher amounts do not have any detrimental effects on the reaction.

The statements regarding temperature, pressure and solvent made above in connection with the reaction of the compounds of formula I apply analogously to this embodiment. However, this variant is preferably carried out at a temperature of about 40° C. to about 70° C. The saturated and aromatic hydrocarbons are especially preferred solvents.

This embodiment provides high yields. Moreover, a double bond optionally present in $R^5$ is preserved. Furthermore, since only the compounds of formula I and their optical antipodes (but not the remaining stereoisomers) react well under the mild temperature conditions mentioned, this embodiment is especially suitable for the manufacture of pure isomeric compounds. $R^5$ in formula Ia above is preferably a $=CH-CH_2-OH$. The double bond in this group is preferably in the trans configuration. Preferred groups of $R^4$ are $-CO-R^6$ and especially $-CO-OR^6$. Especially preferred among such groups are $-CO-OCH_3$, $-CO-OC_2H_5$, $-CO-C_6H_5$ and $-CO-CH_3$.

The compounds of formula I are novel and also form an object of the present invention. They can be prepared in a manner known per se, for example from the corresponding lithium alcoholate (a compound of formula I in which $R^4$ is lithium) by reaction with a corresponding chloride, i.e. with compounds of the formulae $Cl-CO-OR^6$, $Cl-CO-R^6$, $Cl-CO-NR^6R^7$, $Cl-CO-Cl$ or $Cl-SO_2R^6$ in which $R^6$ and $R^7$ are as above. The lithium alcoholates can be obtained in a conventional manner by reacting the corresponding cyclopentanone or cyclohexanone with the corresponding alkynyl lithium. Hydroxy and oxo groups if present are in protected form. These protecting groups can be cleaved off, if desired, before or after the introduction of $R^4$ or after cleavage of $R^4OH$, in accordance with the invention, has been carried out.

The conversion of the compounds of formula II into carotenoids can be carried out in a known manner or conventionally, for example by conversion into suitable aldehydes or phosphonium salts and subsequent Wittig reaction.

The invention is also concerned with all novel compounds, mixtures, processes and uses as herein described.

The invention is illustrated in more detail by the following Examples.

EXAMPLE 1

10.4 g of ethyl (1S,4R,6R)-4-hydroxy-1-(3-hydroxy-1-butynyl)-2,2,6-trimethylcyclohexylcarbonate were dissolved in 50 ml of hot dimethylformamide. The solution was treated with 1 g of pyridinium p-tosylate and the mixture was stirred for 1.5 hours in a pre-heated oil bath (oil bath temperature 90°-93° C., internal temperature about 79°-82° C.). The mixture was subsequently poured into 500 ml of semi-saturated sodium chloride solution and extracted three times with 200 ml of diethyl ether each time. The organic phases were washed once with saturated sodium chloride solution, dried over sodium sulphate and evaporated. The crude product obtained (8.3 g) was chromatographed on silica gel with hexane/diethyl ether (vol. 1:1). There were thus obtained 5.9 g (83.3%) of (4R)-4-(4-hydroxy-2,6,6-trimethyl-1-cyclohexenyl)-3-butyn-2-ol.

The ethyl (1S,4R,6R)-4-hydroxy-1-(3-hydroxy-1-butynyl)-2,2,6-trimethylcyclohexylcarbonate used as the starting material was prepared as follows:

(a) In a four-necked flask equipped with a magnetic stirrer, a thermometer, a dropping funnel and an apparatus for inert gasification 19.52 g of (4R,6R)-4-hydroxy-2,2,6-trimethylcyclohexanone were dissolved under argon in a mixture of 40 ml of absolute tetrahydrofuran and 20 mg of pyridinium p-tosylate and then 14.4 g of isopropenyl methyl ether were added dropwise to the solution within about 20 minutes at 15°-20° C. The solution A obtained was processed as described in paragraph (c).

(b) In a sulphonation flask equipped with a stirrer, a thermometer, a dropping funnel, a rising tube and an apparatus for inert gasification a solution of 23.5 g of 3-butyn-2-yl trimethylsilyl ether in 80 ml of absolute tetrahydrofuran was placed under argon, cooled to $-30°$ C. and treated dropwise within 10 minutes at $-30°$ C. to $-20°$ C. with 105 ml of an about 1.56M solution of butyl lithium in hexane. The mixture was stirred to $-10°$ C. for a further 30 minutes and then again cooled to $-40°$ C. The solution B obtained was processed as described in paragraph (c).

(c) Solution A was added dropwise at $-40°$ C. within 10 minutes to solution B. The mixture was stirred at $-40°$ C. for a further 30 minutes, then treated with 15.7 ml of ethyl chloroformate and the mixture was warmed to room temperature within 1 hour while stirring. The mixture was subsequently cooled to 0° C., treated while stirring with 100 ml of 3N sulphuric acid and stirred at 0°-5° C. for a further 30 minutes. The mixture was diluted with 250 ml of ethyl acetate and the aqueous phase was separated. The aqueous phase was back-extracted twice with 250 ml of ethyl acetate each time. The organic phases were washed three times with 250 ml of saturated sodium hydrogen carbonate solution each time and once with 250 ml of saturated sodium chloride solution, combined and dried over sodium sulphate. After filtering off the drying agent and concentrating the filtrate on a rotary evaporator (water bath temperature 50° C.), there were obtained 43.6 g of crude product which was chromatographed on silica gel with hexane/diethyl ether (vol. 1:1). From the product-containing fractions there was obtained a total of 36.5 g (97.8%) of ethyl (1S,4R,6R)-4-hydroxy-1-(3-hydroxy-1-butynyl)-2,2,6-trimethylcyclohexylcarbonate as a slightly yellowish oil.

EXAMPLE 2

In a two-necked flask equipped with a magnetic stirrer, a thermometer, a reflux condenser and an argon headpiece 6.7 g of imidazole were dissolved under argon in 40 ml of triethylene glycol dimethyl ether and the solution was heated to 195° C. in an oil bath. A solution of 8.0 g of ethyl (1S,4R,6R)-4-hydroxy-1-(5-hydroxy-3-methyl-3E-penten-1-ynyl)-2,2,6-trimethylcyclohexylcarbonate in 15 ml of triethylene glycol dimethyl ether was subsequently added dropwise within 60 minutes at an internal temperature of 188°-190° C. The mixture was held at the same temperature for a further 30 minutes and then poured on to 200 ml of ice/water. The aqueous phase was extracted twice with 250 ml of diethyl ether each time. The combined ether phases were washed four times with 100 ml of water each time, dried over sodium sulphate, concentrated on a rotary evaporator at about 50° C. and then dried at room temperature for 3 hours in a high vacuum. The crude product obtained (6.0 g) was chromatographed on silica gel with diethyl ether/hexane (vol. 1:1), whereby there could be isolated 3.5 g (61.4%) of (4R)-5-(4-hydroxy-2,6,6-trimethyl-1-cyclohexenyl)-3-methyl-2-penten-4-yn-1-ol as a slightly yellowish oil (ratio 2E/2Z=91.0:4.7).

The ethyl (1S,4R,6R)-4-hydroxy-1-(5-hydroxy-3-methyl-3E-penten-1-ynyl)-2,2,6-trimethylcyclohexylcarbonate used as the starting material was prepared as follows:

(a) In a four-necked flask equipped with a magnetic stirrer, a thermometer, a dropping funnel and an apparatus for inert gasification 52.0 of (4R,6R)-4-hydroxy-2,2,6-trimethylcyclohexanone were dissolved under argon in 65 ml of tetrahydrofuran and 50 mg of pyridinium p-tosylate and the solution was treated dropwise at 15°-20° C. within 20 minutes with 48.0 g of isopropenyl methyl ether. The yellowish solution A obtained was processed directly as described in paragraph (c).

(b) In a sulphonation flask equipped with a stirrer, a thermometer, a dropping funnel, a rising tube and an apparatus for inert gasification a solution of 79 g of 5-(2-methoxy-2-propyl)oxy-3-methyl-3E-penten-1-yne in 50 ml of absolute tetrahydrofuran was placed under argon and cooled to −20° C. This solution was now treated dropwise at −30° C. to −20° C. within 20 minutes with 280 ml of an about 1.56M solution of butyl lithium in hexane and the resulting mixture was stirred for a further 30 minutes. The orange solution B obtained was processed as described in paragraph (c).

(c) Solution B was treated dropwise at −15° C. within 20 minutes with solution A and the mixture was stirred at room temperature for a further 2 hours. The mixture was cooled to −20° C., treated while stirring with 42 ml of ethyl chloroformate and the mixture obtained was then warmed to room temperature during 1 hour. The mixture was subsequently diluted with 250 ml of diethyl ether and the aqueous phase was separated and back-washed with 250 ml of diethyl ether. The organic phases were washed twice with 250 ml of saturated sodium chloride solution each time, combined and dried over sodium sulphate. After filtering off the drying agent and concentrating the filtrate on a rotary evaporator (water bath temperature 50° C.), there was obtained 181.5 g of crude ethyl (1S,4R,6R)-4-(2-methoxy-2-propyl)oxy-1-[5-(2-methoxy-2-propyl)oxy-3-methyl-3E-penten-1-ynyl]-2,2,6-trimethylcyclohexylcarbonate was a brown-yellow oil.

(d) The brown-yellow oil obtained was dissolved in 450 ml of tetrahydrofuran and 50 ml of water (turbid solution), treated with 2 g of pyridinium p-tosylate and stirred for a further 20 minutes (clear solution). The brown-orange solution was subsequently treated with 2 g of solid potassium carbonate and evaporated to constant weight on a rotary evaporator (bath temperature 50° C.). The residue was diluted with 250 ml of diethyl ether and extracted with 250 of water. The aqueous phase was separated and back-extracted with 250 ml of diethyl ester. The organic phases were washed twice with 250 ml of saturated sodium chloride solution each time, combined and dried over sodium sulphate. After filtering off the drying agent and concentrating the filtrate on a rotary evaporator (water bath temperature 50° C.), there were obtained 140 g of crude product which was chromatographed on silica gel with diethyl ether/hexane (vol. 1:1). From the product-containing fractions there was obtained a total of 99.0 g (91.6%) of pure ethyl (1S,4R,6R)-4-hydroxy-1-(5-hydroxy-3-methyl-3E-penten-1-ynyl)-2,2,6-trimethylcyclohexylcarbonate as a slightly yellowish oil.

EXAMPLE 3

In a two-necked flask equipped with a magnetic stirrer, a reflux condenser and an argon headpiece 4.4 g of imidazole were dissolved under argon in 50 ml of triethylene glycol dimethyl ether and the solution was heated to 195° C. in an oil bath. A solution of 5 g of ethyl 1-(5-hydroxy-3-methyl-3E-penten-1-ynyl)-2,2,6-trimethylcyclohexylcarbonate in 10 ml of triethylene glycol dimethyl ether was subsequently added dropwise within about 20 minutes at an internal temperature of 185°-190° C. The mixture was held at the same temperature for a further 1 hour and then poured on to 200 ml of ice/water. The aqueous phase was extracted twice with 250 ml of diethyl ether each time. The combined ether phases were washed four times with 100 ml of water each time, dried over sodium sulphate, concentrated on a rotary evaporator at about 40° C. and then dried at room temperature for 2 hours in a high vacuum. The crude product obtained (3.6 g) was chromatographed on silica gel with diethyl ether/hexane (vol. 1:1). From the product-containing fractions there were obtained 2.1 g (59.5%) of 5-(2,6,6-trimethyl-1-cyclohexenyl)-3-methyl-2-penten-4-yn-1-ol as a slightly yellowish oil (ratio 2E/2Z=98.8:0.6).

The ethyl 1-(5-hydroxy-3-methyl-3E-penten-1-ynyl)-2,2,6-trimethylcyclohexylcarbonate used as the starting material was prepared as follows:

(a) 115.1 g of 5-(2-methoxy-2-propyl)oxy-3-methyl-3E-penten-1-yne and 90 ml of tetrahydrofuran were placed in a sulphonation flask equipped with a stirrer, a thermometer, a dropping funnel and an argon headpiece, the mixture was cooled to −25° C. and treated dropwise at this temperature within 20 minutes with a 1.6M solution of butyl lithium in hexane. The mixture was stirred at 0° C. for a further 15 minutes, then cooled to −10° C. and treated dropwise at this temperature within 15 minutes with 72.9 g of 2,2,6-trimethylcyclohexanone. The mixture was subsequently warmed to room temperature and stirred for a further 2 hours. The mixture was cooled to 0° C., treated dropwise at this temperature within 15 minutes with 67.5 ml of ethyl chloroformate, left to warm to room temperature and stirred for a further 1.5 hours. The mixture was subsequently poured into 1 l of saturated sodium hydrogen carbonate solution and extracted twice with 1 l of diethyl ether each time. The organic phases were washed with 1 l of deionized water, dried over sodium sulphate, the drying agent was filtered off and the filtrate was concentrated in vacuo on a rotary evaporator (bath temperature about 45° C.). The residue was freed from 5-(2-methoxy-2-propyl)oxy-3-methyl-3E-penten-1-yne in a high vacuum at a bath temperature of 60° C. during 1 hour. There were obtained 232.1 g (117.3%) of crude ethyl 1-[5-(2-methoxy-2-propyl)oxy-3-methyl-3E-penten-1-ynyl]-2,2,6-trimethylcyclohexylcarbonate which was processed directly without further purification.

(b) 105.0 g of the crude product obtained as described in paragraph (a) were dissolved in 630 ml of tetrahydrofuran in a sulphonation flask equipped with a stirrer, a thermometer and an argon headpiece, the solution was treated with 105 ml of deionized water and 5.25 g of pyridinium p-tosylate and the mixture was stirred at room temperature for a further 30 minutes. The mixture was poured into 750 ml of saturated sodium hydrogen carbonate solution and extracted three times with 600 ml of diethyl ether each time. The organic phases were washed with 750 ml of semi-saturated sodium hydrogen carbonate solution, dried over sodium sulphate, the drying agent was filtered off and the filtrate was concentrated in vacuo on a rotary evaporator (bath temperature about 45° C.). After drying in a high vacuum, there were obtained 84.8 g (116.9%) of crude product which was chromatographed on silica gel with hexane/diethyl ether (vol. 2:1). There were thus obtained 2.3 g (4.5%) of 5-(2,6,6-trimethyl-1-cyclohexenyl)-3-methyl-2-penten-4-yn-1-ol and 53.6 g (73.9%) of ethyl 1-(5-hydroxy-3-methyl-3E-penten-1-ynyl)-2,2,6-trimethylcyclohexylcarbonate.

EXAMPLE 4

In a sulphonation flask equipped with a stirrer, a thermometer, a dropping funnel, a reflux condenser and an apparatus for inert gasification 16 ml of tert.butanol and 20 ml of absolute toluene were placed under argon and cooled to −25° C. This solution was treated dropwise at −30° C. to −20° C. within 10 minutes with 52 ml of a 1.56M solution of butyl lithium in hexane and the mixture was stirred for a further 30 minutes without cooling. There was subsequently added to the thus-prepared solution of lithium tert.-butylate at about 20° C. in one portion a solution of 14.4 g of (1S,4R,6R)-4-hydroxy-1-(5-hydroxy-3-methyl-3E-penten-1-ynyl)-2,2,6-trimethylcyclohexyl benzoate in 120 ml of absolute toluene. The suspension obtained was heated carefully to 65° C. with the aid of an oil bath and stirred at this temperature for 1.5 hours. Thereafter, the mixture was poured on to 150 ml of ice/water. The aqueous phase was separated and extracted twice with 150 ml of diethyl ether each time. The organic phases were washed with 150 ml of saturated sodium chloride solution, combined, dried over sodium sulphate and concentrated on a rotary evaporator at about 40° C. and the residue was then dried at room temperature for 1 hour in a high vaccum. The crude product obtained (12.0 g) was chromatographed on silica gel with diethyl ether/hexane (vol. 1:1). From the product-containing fractions there was obtained a total of 7.5 g (80%) of (4R)-5-(4-hydroxy-2,6,6-trimethyl-1-cyclohexen-1-yl)-3-methyl-2E-penten-4-yn-1-ol as yellowish crystals (purity 98.8%, content of 2Z isomer 1.1%).

The (1S,4R,6R)-4-hydroxy-1-(5-hydroxy-3-methyl-3E-penten-1-ynyl)-2,2,6-trimethylcyclohexyl benzoate used as the starting material was prepared as follows:

(a) A solution of 16.4 g of (4R,6R)-4-hydroxy-2,2,6-trimethylcyclohexanone and 30 mg of pyridinium p-tosylate in 20 ml of tetrahydrofuran was treated dropwise under argon at 15°-20° C. within 10 minutes with 16.0 g of isopropenyl methyl ether.

(b) A solution of 27 g of 5-(2-methoxy-2-propyl)oxy-3-methyl-3E-penten-1-yne in 30 ml of absolute tetrahydrofuran was cooled to −20° C. under argon, then treated dropwise at −30° C. to −20° C. within 10 minutes with 90 ml of an about 1.56M solution of butyl lithium in hexane and the mixture was stirred for a further 30 minutes.

(c) The solution obtained as described in paragraph (b) was treated dropwise at −15° C. within 15 minutes with the solution prepared as described in paragraph (a) and the mixture was stirred at room temperature for a further 1 hour. The mixture was cooled to −10° C., treated while stirring with 18.6 ml of benzoyl chloride and then stirred at room temperature overnight (18 hours). Thereafter, the mixture was poured into 200 ml of saturated sodium hydrogen carbonate solution, the aqueous phase was separated and back-extracted twice with 300 ml of diethyl ether each time. The organic phases were washed twice with 250 ml of saturated sodium chloride solution each time, concentrated, dried over sodium sulphate and the drying agent was filtered off. After concentrating the filtrate on a rotary evaporator (water bath temperature 40° C.), crude (1S,4R,6R)-4-(2-methoxy-2-propyl)oxy-1-[5-(2-methoxy-2-propyl)oxy-3-methyl-3E-penten-1-ynyl]-2,2,6-trimethylcyclohexyl benzoate was obtained as a brown-yellow oil.

(d) The brown-yellow oil obtained was dissolved in 400 ml of tetrahydrofuran and 20 ml of water (turbid solution), treated with 1 g of pyridinium p-tosylate and stirred for a further 15 minutes (clear solution). The mixture was subsequently poured into 200 ml of saturated sodium hydrogen carbonate solution, the aqueous phase was separated and extracted twice with 300 ml of diethyl ether each time. The organic phases were combined, dried over sodium sulphate and the drying agent was filtered off. After concentrating the filtrate on a rotary evaporator (bath temperature 40° C.), there were obtained 51.3 g of crude product which was chromatographed on silica gel with diethyl ether/hexane (vol. 2:1). From the product-containing fractions there was obtained a total of 32.2 g (86.1%) of pure (1S,4R,6R)-4-hydroxy-1-(5-hydroxy-3-methyl-3E-penten-1-ynyl)-2,2,6-trimethylcyclohexyl benzoate as a light yellow oil.

EXAMPLE 5

In a sulphonation flask equipped with a stirrer, a thermometer, a dropping funnel, a reflux condenser and an apparatus for inert gasification 40 ml of tert.butanol and 50 ml of absolute toluene were placed under argon and cooled to −25° C. This solution was treated dropwise at −30° C. to −20° C. within 10 minutes with 130 ml of a 1.56M solution of butyl lithium in hexane and the mixture was stirred for a further 30 minutes without cooling. There was subsequently added to the thus-prepared solution of lithium tert.butylate at 6° C. in one portion a solution of 32.4 g of ethyl (1S,4R,6R)-4-hydroxy-1-(5-hydroxy-3-methyl-3E-penten-1-ynyl)-2,2,6-trimethylcyclohexylcarbonate (prepared according to Example (2) in 150 ml of absolute toluene. The mixture was heated carefully to 55° C. with the aid of an oil bath and stirred at this temperature for 30 minutes. Thereafter, the mixture was poured on to 400 ml of ice/water. The aqueous phase was separated and extracted twice with 300 ml of diethyl ether each time. The organic phases were washed with 300 ml of saturated sodium chloride solution, combined, dried over sodium sulphate and concentrated on a rotary evaporator at about 40° C. and the residue was then dried at room temperature for 5 hours in a high vacuum. There were thus obtained 23.9 g (102.1%) of a yellow-orange crystalline product of (4R)-5-(4-hydroxy-2,6,6-trimethyl-1-cyclohexenyl)-3-methyl-2-penten-4-yn-1-ol (containing 90.5% of 2E isomer with 1.4% of 2Z isomer) which was chromatographed on silica gel with diethyl ether/hexane (vol. 1:1). From the product-containing fractions there was obtained a total of 19.9 g (85%) of (4R)-5-(4-hydroxy-2,6,6-trimethyl-1-cyclohexen-1-yl)-3-methyl-2E-penten-4-yn-1-ol as yellowish crystals (purity 98.0%, content of 2Z isomer 0.5%).

I claim:

1. A compound of the formula

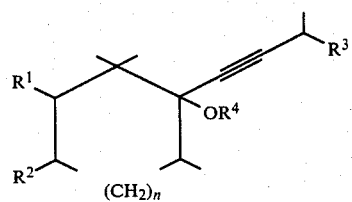

I wherein n is either 0 or 1; one of $R^1$ or $R^2$ is hydrogen and the other is hydrogen, hydroxy, oxo group, or a protected hydroxy or protected oxo group; $R^3$ is hydroxy, oxo group, =CH—CH$_2$—OH or =CH—CHO or one of the foregoing groups where the hydroxy or oxo functions are protected; $R^4$ is $-CO-OR^6$, $-CO-R^6$, $-CO-NR^6R^7$, $-CO-Cl$ or $-SO_2-R^6$; $R^6$ is saturated or aromatic hydrocarbon; and $R^7$ is saturated or aromatic hydrocarbon or hydrogen.

2. The compound of claim 1, wherein $R^4$ is $-CO-OR^6$, $-CO-R^6$, $-CO-OC_2H_5$ or $-CO-C_6H_5$.

3. The compound of claim 1, wherein n is 1 and $R^1$ is hydrogen.

4. The compound of claim 1, wherein one of $R^1$ or $R^2$ is hydrogen and the other is hydrogen or hydroxy.

5. A compound of the formula

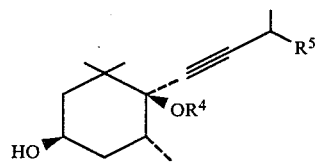

Ia wherein $R^5$ is hydroxy or $=CH-CH_2-OH$ and $R^4$ is $-CO-OR^6$, $-CO-R^6$, $-CO-NR^6R^7$, $-CO-Cl$ or $-SO_2-R^6$; $R^6$ is saturated or aromatic hydrocarbon; and $R^7$ is saturated or aromatic hydrocarbon or hydrogen, or the optical antipode thereof.

6. A compound of the formula

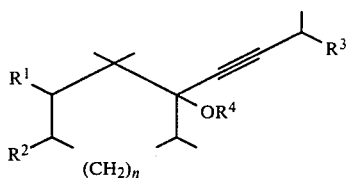

wherein n is either 0 or 1; one of $R^1$ or $R^2$ is hydrogen and the other is hydrogen, hydroxy, oxo group, or a protected hydroxy or protected oxo group; $R^3$ is hydroxy or $=CH-CH_2-OH$; $R^4$ is $-CO-OR^6$, $-CO-R^6$, $-CO-NR^6R^7$, $-CO-Cl$ or $-SO_2-R^6$; $R^6$ is saturated or aromatic hydrocarbon; and $R^7$ is saturated or aromatic hydrocarbon or hydrogen.

7. The compound of claim 6, wherein $R^4$ is $-CO-OR^6$ or $-CO-R^6$.

8. The compound of claim 7, wherein $R^4$ is $-CO-OC_2H_5$ or $-CO-C_6H_5$.

9. The compound of claim 8, wherein n is 1 and $R^1$ is hydrogen.

10. The compound of claim 9, wherein $R^2$ is hydroxy.

11. The compound of claim 10, wherein $R^3$ is hydroxy or $=CH_2-CH_2-OH$.

* * * * *